US006210933B1

(12) United States Patent
Gilbert et al.

(10) Patent No.: US 6,210,933 B1
(45) Date of Patent: Apr. 3, 2001

(54) RECOMBINANT α-2,3-SIALYLTRANSFERASES AND THEIR USES

(75) Inventors: Michel Gilbert, Hull; Warren W. Wakarchuk; N. Martin Young, both of Gloucester, all of (CA); Michael P. Jennings, Brisbane (AU); Edward Richard Moxon, Oxford (GB)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/387,942

(22) Filed: Sep. 1, 1999

Related U.S. Application Data

(62) Division of application No. 08/872,485, filed on Jun. 7, 1997, now Pat. No. 6,096,529.
(60) Provisional application No. 60/019,520, filed on Jun. 10, 1996, now abandoned.

(51) Int. Cl.[7] .............................. C12N 9/10; C12N 15/54; C12D 19/18
(52) U.S. Cl. ......................... 435/97; 435/193; 536/23.2
(58) Field of Search ...................... 435/193, 97; 536/23.2

(56) References Cited

U.S. PATENT DOCUMENTS 5,545,553   8/1996   Gotschlich ...................... 435/252.33

OTHER PUBLICATIONS

Frosch et al. (1991) *Mol. Microbiol.* 5: 1251–1263.
Jennings et al. (1995) *Mol. Microbial.* 18: 729–740.
Kajihara et al. (1996) *J. Org. Chem.* 61: 8632–8635.
MacKenzie et al. (1994) *Bio/Technology* 12: 390–395.
Mandrell et al. (1993) *Microb. Pathog.* 14: 315–327.
McLaughlin et al. (1992) *J. Bacteriol.* 174: 6455–6459.
Moran et al. (1996) *FEMS Immunol. Med. Microbiol.* 16: 105–115.
Pavliak et al. (1993) *J. Biol. chem.* 268: 14146–14152.
Preston et al. (1996) *Crit. Rev. Microbiol.* 22 139–180.
Reuter et al. (1996) *Biol. Chem. Hoppe–Seyler* 377: 325–342.
Smith et al. (1992) *FEMS Microbiol Lett.* 100: 287–292.
Tsuji et al. (1996) *Glycobiology* 6:v–vii.
Vogel et al. (1996) *Med. Microbiol. Immunol.* 186: 81–87.
Weisgerber et al. (1991) *Glycobiol.* 1: 357–365.
Yamamoto et al. (1996) *J. Biochem.* 120: 104–110.

*Primary Examiner*—Rebecca E. Prouty
(74) *Attorney, Agent, or Firm*—Townsend and Townsend and Crew LLP

(57) ABSTRACT

The structure and specificity of the recombinant α-2,3-sialyltransferases from Neisseria spp, are disclosed. Their use in the production of desired carbohydrate structures is also provided.

12 Claims, 2 Drawing Sheets

A

B

RECOMBINANT α-2,3-SIALYLTRANSFERASES AND THEIR USES

CROSS REFERENCE TO RELATED APPLICATIONS

This application is a division of and claims the benefit of U.S. Ser. No. 08/872,485, filed Jun. 7, 1997 now U.S. Pat. No. 6,096,529, which claims the benefit of U.S. Ser. No. 60/019,520, filed Jun. 10, 1996 now abandoned, which is incorporated, in its entirety, herein by reference.

BACKGROUND OF THE INVENTION

Sialyltransferases are a group of glycosyltransferases that transfer sialic acid from an activated sugar nucleotide to acceptor oligosaccharides found on glycoproteins, glycolipids or polysaccharides. Sialylated oligosaccharides play important roles in cell-cell recognition, cell differentiation and various receptor-ligand interactions in mammalian systems. The large number of sialylated oligosaccharide structures has lead to the characterization of many different sialyltransferases involved in the synthesis of these structures. Based on the linkage and acceptor specificity of the sialyltransferases studied so far, it has been determined that at least 13 distinct sialyltransferase genes are present in mammalian systems (Tsuji, S. et al. (1996) *Glycobiology* 6:v–vii).

Sialylated glycoconjugates are also found in bacteria (Preston, A. et al. (1996) *Crit. Rev. Microbiol.* 22:139–180; Reuter, G. et al. (1996) *Biol. Chem. Hoppe-Seyler* 377:325–342) are thought to mimic oligosaccharides found in mammalian glycolipids to evade the host immune response (Moran, A. P. et al. (1996) *FEMS Immunol. Med. Microbiol.* 16:105–115). The importance of sialylated lipooligosaccahride (LOS) in the pathogenesis of *Neisseria gonorrhoeae* has been established (Smith et al., (1992) *FEMS Microbiol Lett.* 100:287–292) while for *N. meningitidis* both the polysialic acid capsule and the sialylated LOS were found to be important for pathogenicity (Vogel, U. et al. (1996) *Med. Microbiol. Immunol.* 186:81–87).

Despite their importance as proven or potential virulence factors, few bacterial sialyltransferases have been cloned (Weisgerber, C. et al. (1991) *Glycobiol.* 1:357–365; Frosch, M. et al. (1991) *Mol. Microbiol.* 5:1251–1263; Gilbert, M. et al. (1996) *J. Biol. Chem.* 271:28271–28276) or purified (Yamamoto, T. et al. (1996) *J. Biochem.* 120:104–110). The α-2,8-sialyltransferases involved in the synthesis of the polysialic acid capsules have been cloned and expressed from both *Escherichia coli* (Weisgerber, C. et al. (1991) *Glycobiol.* 1:357–365) and *N. meningitidis* (Frosch, M. et al. (1991) *Mol. Microbiol.* 5:1251–1263). Glycosyltransferases from *N. gonorrhoeae* involved in the synthesis of lipooligosaccharide (LOS) have been cloned (U.S. Pat. No. 5,545,553).

Because of biological activity of their products, mammalian sialyltransferases generally act in specific tissues, cell compartments and/or developmental stages to create precise sialyloglycans. Bacterial sialyltransferases are not subject to the same constraints and can use a wider range of acceptors than that of the mammalian sialyltransferases. For instance, the α-2,6-sialyltransferase from *Photobacterium damsela* has been shown to transfer sialic acid to terminal galactose residues which are fucosylated or sialylated at the 2 or 3 position, respectively (Kajihara, Y. et al. (1996) *J. Org. Chem.* 61:8632–8635). Such an acceptor specificity has not been reported so far for mammalian sialyltransferases.

Bacterial glycosyltransferases are useful in a number of applications, such as the synthesis of desired oligosaccharides with biological activity. Identification and characterization of new bacterial glycosyltransferases is thus useful in the development of these technologies. The present invention provides these and other advantages.

SUMMARY OF THE INVENTION

The present invention provides isolated nucleic acid molecules comprising a polynucleotide sequence which encodes an α2,3-sialyltransferase polypeptide and which hybridizes to SEQ. ID. NOS: 1 or 3 under stringent conditions. Typically, the polynucleotide sequence encodes a α2,3-sialyltransferase polypeptide having a molecular weight of about 40 kD, for instance as shown in SEQ. ID. NOS: 2 or 4. Exemplified polynucleotide sequences are shown in SEQ. ID. NOS: 1 and 3. The nucleic acid molecule may be isolated from *Neisseria meningitidis* or *N. gonorrhoeae*.

If expression of the enzyme is desired, the nucleic acid molecules of the invention may further comprise an expression containing a promoter sequence operably linked to the polynucleotide sequence. In some embodiments, the promoter is active in prokaryotic cells, such as *E. Coli*. Also provided are cells (e.g., *E. coli*) comprising the recombinant expression cassette of the invention.

The invention further provides methods of adding a sialic acid residue to an acceptor molecule comprising a terminal galactose residue. The methods comprise contacting the acceptor molecule with an activated sialic acid molecule and an α2,3-sialyltransferase of the invention. The terminal galactose residue may linked through an α or a β linkage to a second residue in the acceptor molecule. Exemplary linkages include β1,4 and β1,3 linkages. The activated sialic acid is typically CMP-Neu5Ac.

Definitions

The sialyltransferases of the invention are useful for transferring a monosaccharide from a donor substrate to an acceptor molecule. The addition generally takes place at the non-reducing end of an oligosaccharide or carbohydrate moiety on a biomolecule. Biomolecules as defined here include but are not limited to biologically significant molecules such as carbohydrates, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalacto;
Glc=glucosyl;
GlcNAc=N-acetylglico;
Man=mannosyl; and
NeuAc=sialyl (N-acetylneuraminyl).

The sialyltransferases of the invention can be used to add sialic acid residues of different forms to acceptor molecules. Typically, the sialic acid is 5-N-acetylneuraminic acid, (NeuAc) or 5-N-glcolylneuraminic acid (NeuGc). Other sialic acids may be used in their place, however. For a review of different forms of sialic acid suitable in the present invention see, Schauer, *Methods in Enzymology*, 50: 64–89 (1987), and Schaur, *Advances in Carbohydrate Chemistry and Biochemistry*, 40: 131–234.

Donor substrates for glycosyltransferases are activated nucleotide sugars. Such activated sugars generally consist of uridine, guanosine, and cytidine diphosphate derivatives of the sugars in which the nucleoside diphosphate serves as a leaving group. The donor substrate for the sialyltransferases of the invention are activated sugar nucleotides comprising the desired sialic acid. For instance, in the case of NeuAc, the activated sugar is CMP-NeuAc.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

Much of the nomenclature and general laboratory procedures required in this application can be found in Sambrook, et al., *Molecular Cloning: A Laboratory Manual* (2nd Ed.), Vol. 1–3, Cold Spring Harbor Laboratory, Cold Spring Harbor, N.Y., 1989. The manual is hereinafter referred to as "Sambrook et al."

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

A "sialyltransferase polypeptide" of the invention is sialyltransferase protein or fragment thereof that is capable of catalyzing the transfer of a sialic acid from a donor substrate (e.g., CMP-NeuAc) to an acceptor molecule. Typically, such polypeptides will be substantially similar to the exemplified proteins disclosed here.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" is meant to refer to material which is substantially or essentially free from components which normally accompany the enzyme as found in its native state. Thus, the enzymes of the invention dc not include materials normally associated with their in situ environment. Typically, isolated proteins of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The term "identical" in the context of two nucleic acids or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48:443, by the search for similarity method of Pearson and Lipman (1988) *Proc. Natl. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

An additional algorithm that is suitable for determining sequence similarity is the BLAST algorithm, which is described in Altschul et al. (1990) *J. Mol. Biol.* 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915–10919) alignments (B) of 50, expectation (E) of 10, M=5, N=−−4, and a comparison of both strands.

The BLAST algorithm performs a statistical analysis of the similarity between two sequences; see, e.g., Karlin and Altschul (1993) *Proc. Nat'l. Acad. Sci. USA* 90: 5873–5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a glycosyltransferase gene or cDNA if the smallest sum probability in a comparison of the test nucleic acid to a glycosyltransferase nucleic acid is less than about 1, preferably less than about 0.1, more preferably less than about 0.01, and most preferably less than about 0.001.

The term "substantial identity" or "substantial similarity" in the context of a polypeptide indicates that a polypeptides comprises a sequence with at least 70% sequence identity (or similarity) to a reference sequence, or preferably 80%, or more preferably 85% sequence identity (or similarity) to the reference sequence, or most preferably 90% identity (or similarity) over a comparison window of about 10–20 amino acid residues. An indication that two polypeptide sequences are substantially identical or similar is that one peptide is immunologically reactive with antibodies raised against the second peptide.

An indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 50° C. lower than the thermal melting point (Tm), for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual,* Cold Spring Harbor Publications, New York, for a description of immunoassay formats and conditions that can be used to determine specific immunoreactivity.

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following is six groups each contain amino acids that are examples of conservative substitutions for one another:

1) Alanine (A), Serine (S), Threonine (T);
2) Aspartic acid (D), Glutamnic acid (E);
3) Asparagine (N), Glutamnine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins,* W. H. Freeman and Company. In addition, individual substitutions, deletions or additions which alter, add or delete a single amino acid or a small percentage of amino acids in an encoded sequence are also "conservatively modified variations".

BRIEF DESCRIPTION OF THE DRAWINGS

FIG. 2A: When the 8-aminopyrene-1,4,6-trisulphonic acid is reducively aminated onto reducing disaccharides, the reducing end is ring-opened. R1=OH (NAc when R2=LacNAc); R2=Gal-α, Gal-β-1 N-acetyllactosamine: Lacto-N-neotetraose; Lacto-N-tetraose; Gal-α-(1→4)-Gal-β(1→4). FIG. 2B: R=Gal-α-; Gal-β; Lactose; N-acetyllactosamine; Gal-α-(1→4)-Gal-β-(1→4).

DESCRIPTION OF THE PREFERRED EMBODIMENT

Figure 1:
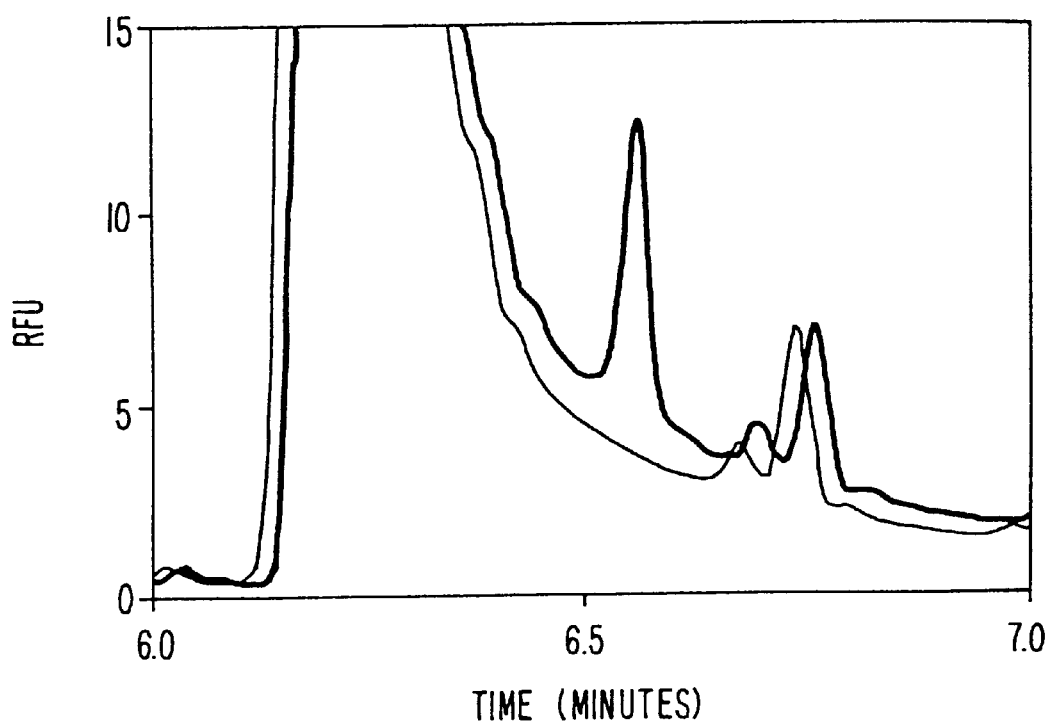
FIG. 1 shows two electropherograms superimposed to illustrate the level of sialyltransferase activity found in a 1.5 ml *E. coli* culture infected with 1000 pfu from the genomic DNA bank of *N. meningitidis* in λZAPII. The thin line is from a run where the reaction contained no CMP-Neu5Ac donor, and the thick line is from a run containing the CMP-Neu5Ac donor. The peak at 6.6 minutes was shown to comigrate with FCHASE-α-2,3-sialyl-N-acetyllactosamine.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Sambrook et al. (1989) *Molecular Cloning: A Laboratory Manual, 2nd Ed., Vols.* 1–3, Cold Spring Harbor Laboratory; Berger and Kimmel, *Guide to Molecular Cloning Techniques, Methods in Enymology* volume 152 Academic Press, Inc., San Diego, Calif.; and *Current Protocols in Molecular Biology,* F. M. Ausubel et al., eds., Current Protocols, a joint venture between Greene Publishing Associates, Inc. and John Wiley & Sons, Inc., (1994 Supplement).

Preparation of Nucleic Acids of the Invention

Nucleic acids encoding sialyltransferases polypeptides of this invention can be prepared by any suitable method known in the ant, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066.

In one preferred embodiment, a nucleic acid encoding a sialyltransferase is isolated by routine cloning methods. A nucleotide sequence of a sialyltransferase as provided herein, is used to provide probes that specifically hybridize to a sialyltransferase gene in a genomic DNA sample, or to a sialyltransferase mRNA in a total RNA sample (e.g., in a Southern or Northern blot). Once the target sialyltransferase nucleic acid is identified, it can be isolated according to standard methods known to those of skill in the art.

The desired nucleic acids can also be cloned using well known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook., and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039. Suitable primers for use in the amplification of the nucleic acids of the invention are described in the Example Section, below.

The sialyltransferase nucleic acid can also be cloned by detecting its expressed product by means of assays based on the physical, chemical, or immunological properties of the expressed protein. For example, one can identify a cloned sialyltransferase nucleic acid by the ability of a polypeptide encoded by the nucleic acid to catalyze the transfer of a sialic acid from a donor to an acceptor moiety. In a preferred method, capillary electrophoresis is employed to detect the reaction products. This highly sensitive assay involves using either monosaccharide or disaccharide aminophenyl derivatives which are labeled with fluorescein as described below and in Wakarchuk et al. (1996) *J. Biol. Chem.* 271 (45): 28271–276.

In some embodiments, it may be desirable to modify the sialyltransferase nucleic acids of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734.

Preparation of Expression Cassettes Encoding Sialyltransferases of the Invention The sialyltransferases sequences of the invention are incorporated into expression cassettes for high level expression in a desired host cell. A typical expression cassette contains a promoter operably linked to the desired DNA sequence. More than one sialyltransferase polypeptide may be expressed in a single prokaryotic cell by placing multiple transcriptional cassettes in a single expression vector, or by utilizing different selectable markers for each of the expression vectors which are employed in the cloning strategy.

Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21–25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

Either constitutive or regulated promoters can be used in the present invention. Regulated promoters can be advantageous because the host cells can be grown to high densities before expression of the sialyltransferase polypeptides is induced. High level expression of heterologous proteins slows cell growth in some situations. Regulated promoters especially suitable for use in *E. coli* include the bacteriophage lambda $P_L$ promoter, the hybrid trp-lac promoter (Amann et al., Gene (1983) 25: 167; de Boer et al., *Proc.*

Natl. Acad. Sci. USA (1983) 80: 21, and the bacteriophage 17 promoter (Studier et al., *J. Mol. Biol.* (1986); Tabor et al., (1985). These promoters and their use are discussed in Sambrook et al., supra.

For expression of sialyltransferase polypeptides in prokaryotic cells other than *E. coli,* a promoter that functions in the particular prokaryotic species is required. Such promoters can be obtained from genes that have been cloned from the species, or heterologous promoters can be used. For example, the hybrid trp-lac promoter functions in Bacillus in addition to *E. coli.*

A ribosome binding site (RBS) is conveniently included in the expression cassettes of the invention. An RBS in *E. coli,* for example, consists of a nucleotide sequence 3–9 nucleotides in length located 3–11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297–16302.

The sialyltransferase polypeptides can be expressed intracellularly, or can be secreted from the cell. Intracellular expression often results in high yields. If necessary, the amount of soluble, active sialyltransferase polypeptide may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the sialyltransferase polypeptides are secreted from the cell, either into the periplasin or into the extracellular medium, the DNA sequence is linked to a cleavable signal peptide sequence. The signal sequence directs translocation of the sialyltransferase polypeptide through the cell membrane. An example of a suitable vector for use in *E. coli* that contains a promoter-signal sequence unit is pTA 1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670).

The sialyltransferase polypeptides of the invention can also be produced as fusion proteins. This approach often results in high yields, because normal prokaryotic control sequences direct transcription and translation. In *E. coli,* lacZ fusions are often used to express heterologous proteins. Suitable vectors are readily available, such as the pUR, pEX, and pMR100 series (see, e.g., Sambrook et al., supra.). For certain applications, it may be desirable to cleave the non-sialyltransferase amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

A suitable system for obtaining recombinant proteins from *E. coli* which maintains the integrity of their N-termini has been described by Miller et al. *Biotechnology* 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

Expression of Sialyltransferases of the Invention

Sialyltransferases of the invention can be expressed in a variety of host cells, including *E. coli,* other bacterial hosts, yeast, and various higher eukaryotic cells such as the COS, CHO and HeLa cells lines and myeloma cell lines. Examples of useful bacteria include, but are not limited to, Escherichia, Entertobacter, Azotobacter, Erwinia, Bacillus, Pseudomonas, Klebsielia, Proteus, Salmonella, Serratia, Shigella, Rhizobia, Vitreoscilla, and Paracoccus. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immnunoglobulin genes, SV40, cytomegalovirus, etc., and a polyadenylation sequence, and may include splice donor and acceptor sequences.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant sialyltransferase polypeptides can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enymology Vol.* 182: *Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

One of skill would recognize that modifications can be made to the glycosyltransferase proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Uses of Sialyltransferases

The invention provides methods of using sialyltransferases produced using the methods described herein to prepare desired oligosaccharides (which are composed of two or more saccharides). The glycosyltransferase reactions of the invention take place in a reaction medium comprising at least one glycosyltransferase, a donor substrate, an acceptor sugar and typically a soluble divalent metal cation. The methods rely on the use of a glycosyl transferase to catalyze the addition of a saccharide to a substrate saccharide. For example, the invention provides methods for adding sialic acid to a galactose residue in an α2,3 linkage, by contacting a reaction mixture comprising an activated sialic acid (e.g., CMP-NeuAc) to an acceptor moiety comprising a Gal residue in the presence of a sialyltransferase that has been prepared according to the methods described herein.

A number of methods of using glycosyltransferases to synthesize desired oligosaccharide structures are known. Exemplary methods are described, for instance, WO 96/32491, Ito et al., *Pure Appl. Chem.*, 65:753 (1993), and U.S. Pat. Nos. 5,352,670, 5,374,541, and 5,545,553.

The sialyltransferase prepared as described herein can be used in combination with additional glycosyltransferases. For example, one can use a combination of sialyltransferase and galactosyltransferases. In this group of embodiments, the enzymes and substrates can be combined in an initial reaction mixture, or preferably the enzymes and reagents for a second glycosyltransferase cycle van be added to the reaction medium once the first glycosyltransferase cycle has neared completion. By conducting two glycosyltransferase cycles in sequence in a single vessel, overall yields are improved over procedures in which an intermediate species is isolated. Moreover, cleanup and disposal of extra solvents and by-products is reduced.

The products produced by the above processes can be used without purification. However, it is usually preferred to recover the product. Standard, well known techniques for recovery of glycosylated saccharides such as thin or thick layer chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins. Nanofiltration or reverse osmosis can then be used to remove salts. Nanofilter membranes are a class of reverse osmosis membranes which pass monovalent salts but retain polyvalent salts and uncharged solutes larger than about 100 to about 700 Daltons, depending upon the membrane used. Thus, in a typical application, saccharides prepared by the methods of the present invention will be retained in the membrane and contaminating salts will pass through. Using such techniques, the saccharides (e.g., sialyl lactose) can be produced at essentially 100% purity, as determined by proton NMR and TLC.

EXAMPLE 1

This example describes the cloning and initial characterization of genes encoding sialyltransferases from *N. meningitidis* and *N. gonorrhoeae*. Cloning was achieved by the use of a highly sensitive screening procedure based on the expression of enzyme activity.

Experimental Procedures

Bacterial Strains—The following *N. meningitidis* strains were used in this study: immunotype L3 MC58 (NRCC #4728); immunotype L3 406Y (NRCC # 4030); immunotype L7 M982B (NRCC #4725). DNA from *N. gonorrhoeae* F62 (ATCC 33084) was a kind gift from Dr. Wendy Johnson (Health Canada, Ottawa).

Basic Recombinant DNA methods—Plasmid DNA isolation, restriction enzyme digestions, the purification of DNA fragments for cloning, ligations, transformations and DNA sequencing were performed as recommended by the enzyme supplier, or the manufacturer of the kit used for the particular procedure. PCR was performed with Pwo polymerase as described by the manufacturer (Boehringer Mannheim, Laval, PQ). Restriction and DNA modification enzymes were purchased from New England Biolabs LTD., Mississauga, Ont. Qiaprep columns were from Qiagen Inc., Chatsworth, Calif., USA. DNA sequencing was performed with an Applied Biosystems (Montreal PQ) model 370A automated DNA sequencer using the manufacture's cycle sequencing kit.

Cloning and Sequencing of the Sialyltransferase from *N. meningitidis*—The genomic library was prepared using 3–5 kb fragments from a HaeIII partial digest of the chromosomal DNA of *N. meningitidis* MC58 into λZAPII (Stratagene, La Jolla, Calif.) as the vector (Jennings, M. P., et al. (1995) *Mol. Microbial.* 18, 729–740). The λZAPII library was plated at low density and 3600 well isolated plaques were picked in pools of 100. Phage suspensions were made as previously described (Sambrook, J., et al. (1989) Molecular Cloning: A Laboratory Manual (2nd ed.) Cold Spring Harbour Laboratory, Cold Spring Harbour, N.Y.) and use to infect 1.5 mL cultures of *E. coli* XL1-Blue (in LB medium with 0.2 maltose, 10 mM $MgSO_4$ and 2 mM IPTG) which were grown for 4.5h. Toluene was added to 1% and the cells were then assayed for sialyltransferase activity as described below. The positive pools were plated, then plaques were picked in pools of 5 and analyzed again for activity. Positive pools of 5 were then used to isolate individual clones expressing sialyltransferase activity. Phagemids carrying the sialyltransferase gene were excised from the positive λZAPII clones using the ExAssist helper phage and the SOLR *E. coli* strain as described by the supplier Stratagene. The DNA sequence for the 2.1 kb insert of pNST-01 was determined, and PCR primers based on this sequence were used to amplify the genes from DNA prepared from *N. meningitidis* 406Y, M982B, and *N. gonorrhoeae* F62. The primer sequences were 5' primer SIALM-5F (SEQ ID NO: 5), (nt 540–569 in NST-01 insert sequence, NdeI site shown in italics) 43 mer 5' C TTA GGA GGT CAT ATG TTC AAT TTG TCG GAA TGG AGT TTT AGG 3', and 3' primer SIALM-16R (SEQ ID NO: 6), (nt 1685–1658 of NST-01 insert sequence, SalI site shown in italics) 42 mer: 5'CC TAG GTC GACTCA TTA ATT TTT ATC GTC AAA TGT CAA AAT C 3'.

Detection of the Sialyltransferase by Western Blotting—The gene product was detected in *E. coli* by first constructing a plasmid consisting of the 1st ORF from pNST-01, and the peptide tag for immunodetection with anti-c-myc antibody as previously described (MacKenzie, R. C., et al. (1994) *Bio/Technology* 12, 390–395). This construct was made using the following primers for PCR amplification, 5' end primer was the standard M13 "reverse" primer, and 3' end primer SIALM-18R (SEQ ID NO: 7): (SalI site in italics, and the c-myc tag in bold) 5' CC TAG GTC GAC TCA TTA GTT CAG GCT TTC TTC GCT GAT CAG TTT TTG TTC ATT TTT ATC GTC AAA TGT CAA AAT CGG G3' 78 MER. The PCR product was cloned in the vector pT7-7 (Tabor, S., et al. (1985) *Proc. Natl. Acad. Sci.* 82, 1074–1078) and protein expression was then induced with IPTG. Western blotting was performed as previously described (MacKenzie, R. C., et al. (1994) *Bio/Technology* 12, 390–395).

Measurement of Sialyltransferase Activity—The sialyltransferase activity from *N. meningitidis* MC58L3, 406Y L3 and M982B L7, and the *E. coli* carrying pNST plasmids was measured in toluene treated cells or cell free extracts prepared as described previously (Wakarchuk, et al. (1996) *J. Biol. Chem.* in Press) acceptors were derived from aminophenylglycosides reacted with 6(5-fluoresceincarboxamido)-hexanoic acid succimidyl ester (FCHASE) and were prepared as previously described (Wakarchuk, et al. (1996) *J. Biol. Chem.* in Press). Reactions for the enzyme were performed at 37° C. in 20 μl of MES buffer, 50 mM pH 6.0, 10 mM $MnCl_2$, with 0.2 or 1.0 mM labeled acceptor, 0.2 mM CMP-Neu5Ac donor and various amounts of enzyme, either from crude bacterial extracts, or extracts of recombinant *E. coli* with the cloned gene. The recombinant enzymes were assayed for 10–120 minutes, while extracts from *N. meningitidis* were incubated 1–15 h. The reactions were terminated by diluting the reaction 1:100 with 10 mM NaOH. These samples were then diluted appropriately in water prior to analysis by capillary electrophoresis.

Capillary electrophoresis (CE) and was performed with a Beckman (Fullerton, Calif.) P/ACE 5510 equipped with a 3 mW Argon-ion laser induced fluorescence detector, λ excitation=488 nm, λ emission=520 nm. The capillary was bare silica 75μx47 cm, with the detector at 40 cm. The capillary was conditioned before each run by washing with 0.2 M NaOH for 2 min., water for 2 min., and 25 mM sodium tetraborate pH 9.4 for 2 min. Samples were introduced by pressure injection for 2–5 seconds, and the separation was performed at 15 kV, 75 μA. Peak integration was performed with the Beckman System Gold (version 8.1) software.

For rapid detection of enzyme activity, samples from the transferase reaction mixtures were examined by thin layer chromatography on silica-60 TLC plates (E. Merck). A spot of 0.5–1.0 μl from the reaction was air dried, and the plate was developed with ethyl acetate/methanol/water/acetic acid 7:2:1:0.1. After drying the acceptor and product spots could be seen by illumination of the plate with a 365 nm UV lamp. The product $R_f$ under these conditions was 0.05.

Preparative Sialyltransferase reactions—Preparative enzyme reactions were performed as coupled enzyme reactions with the cloned *N. meningitidis* CMP-Neu5Ac synthetase. The reactions contained 25 mM HEPES pH 7.5, 0.2 mM dithiothreitol and 10 mM $MgCl_2$, 400 mU/ml of CMP-Neu5Ac synthetase, 300 mU/ml inorganic pyrophosphatase (Sigma), 1.5 mM CTP, 1.5 mM Neu5Ac, and 50 mU of sialyltransferase (based on FCHASE-aminophenyl-LacNAc as the acceptor). The acceptor, FCHASE-aminophenyl-Lac or FCHASE-aminophenyl-LacNAc, was dried down in the tube under vacuum, and the reagents were then added to the tube; the concentration of FCHASE-aminophenylglycoside in these reactions was 1 mM. These reactions were performed at 30° C. for 3–5 h. After the reaction, the FCHASE-aminophenylglycoside was bound to a Sep-Pak C18 reverse phase cartridge (Waters), desalted by washing with water and then eluted in 50% acetonitrile.

Determination of the Linkage Specificity of the Sialyltransferase—The product from a preparative sialyltransferase reaction was examined by NMR Samples for NMR were prepared by the TLC method, and were then freeze dried from $D_2O$ 3 times prior to collection of the spectra. NMR data collection was performed with a Bruker AMX 500 spectrometer. Spectra were recorded at 340 K in 5 mm tubes at a concentration of 0.5–1.0 mg of FCHASE-aminophenylglycoside in 0.5 ml of $D_2O$. The proton chemical shifts in $D_2O$ are expressed relative to the HOD signal (4.348 at 340 K).

Results

Detection and Characterization of α-2,3-Sialyltransferase activity from *N. meningitidis*—The initial part of this work was performed with the *N. meningitidis* strain 406Y L3, which possesses an LOS identical to that of strain MC58, but has a different capsuler type. Both of these strains elaborate the L3 immunotype LOS which consists of a alacto-N-neotetraose branch with an α-2,3 -sialic acid on the terminal galactose residue (Pavliak, V., et al. (1993) *J. Biol. Chem.* 268, 14146–14152). Both of these strains produced easily detectable levels of α-2,3 -sialyl-transferase when using as little as a single colony ($10^7$ cells) with the CE based assay. Crude extract from *N. meningitidis* 406Y L3 was used to prepare material for determination of the linkage of the sialoside being synthesized and the enzyme was verified by NMR of its product to be an β-Galactoside α-2,3-sialyltransferase. By the complete $^1H$ assignment of the compounds was performed. It was found that the $^1H$ chemical shifts were similar to those of reported structures containing α-2,3-Sialyl-Gal structures (Pavliak, V., et al. (1993) *J. Biol. Clem.* 268, 14146–14152). Also an NOE across the glycosidic bond $H_3$—sialic acid to $H_3$ Gal was observed as well as a long range coupling from $C_2$-sialic acid to $H_3$ of Gal confirmed that the α-2,3-Sialyl-Gal linkage was present.

Variation of the reaction conditions showed the enzyme had a pH optimum of 6.0 and the activity was stimulated 2-fold by the addition of either 10 mM $MgCl_2$ or 3-fold by 10 mM $MnCl_2$. However, there are no stringent metal requirements since it was active in the presence of 5 mM EDTA. These same conditions were also optimal for the enzyme from crude extracts of MC58, 406Y and for the recombinant enzymes from MC58. The natural enzyme was mostly associated with the cell membrane fraction (86% in the cell membrane pellet after centrifugation at 100,000×g). However, no detergent was required for activity, and in fact many common detergents tested inhibited the enzyme, with the exception of Triton X-100 up to 0.2%. Using this method no activity could be detected in M982B L7 cells.

Cloning and Sequencing of the Sialyltransferase Gene from *N. meningitidis* MC58—Using the CE-LIF assay, we observed sialyltransferase activity one time out of five when we infected a 2 mL IPTG-induced *E. coli* XL1-Blue culture with 1000 pfu from the *N. meningitidis* MC58 genomic library in λZAPII (FIG. 1). Formation of the product peak in the electropherogram required the addition of CMP-Neu5Ac, and it migrated the same as the sialidase-sensitive product peak formed by the natural enzyme. The peak in the CE electropherogram corresponds to 20 attomoles ($2 \times 10^{-17}$ moles) of product. Single clones expressing the sialyltransferase were obtained by a "divide and conquer" strategy sequentially screening pools of 100 pfu from the λZAPII library of MC58, pools of 5 pfu derived from the first positive pool, and finally individual plaques plated at low density. The initial screening yielded 2 positive pools of 100 pfu out of 36. From one of these pools we screened 60 pools of 5 pfu and obtained 3 positive pools. From the positive pools of 5 pfu we obtained many individual positive clones and the pBluescript SK-phagemids excised from them were found to carry a 2.1 kb insert.

The 2.0 kb insert was sequenced on both strands (GenBank accession No. U60660) and a BLASTX search was performed in GENEBANK in order to identify any homology with previously sequenced genes. This analysis revealed two partial ORF (nt 1–141 and nt 1825–2039) located at the opposite ends of the 2.1 kb insert which were clearly homologous with various bacterial isocitrate dehydrogenases (60–85% identity) and various bacterial cytochrome c' proteins (43–63% identity) respectively. A third ORF (nt 573–1685) was designated lst (lipooligosaccharide sialyltransferase) and revealed significant homology to a Haemophilus influenzae gene designated lsg-ORF2 (Genbank Accession No. M94855). Pair-wise alignment between the translation products of lst and lsg-ORF2 indicated that their aa sequences share 29.3% identity and 56.3% similarity.

The lst gene product has two potential start codons. The second of these is more likely to be used since the sequence immediately following this start codon appears to be a non-cleavable leader sequence (Nakai, K., et al. (1991) *Proteins: Structure, function, and genetics* 11, 95–110), and a potentially very good ribosome binding site (AGGGA) occurs just upstream.

Comparison of sialyltransferase genes from different *N. meningitidis* isolates and *N. gonorrhoeae*—Isolation of the genes from *N. meningitidis* 406Y L3 (GenBank U60661, SEQ. ID. NOS: 1 and 2), M982B L7 (GenBank U60663) and *N. gonorrhoeae* F62 (GenBank U60664, SEQ. ID. NOS: 3 and 4) was accomplished with PCR primers based on the gene from MC58 L3 (GenBank U60660). 12 base differences were found, which results in 5 amino acid differences between the 2 genes from the L3 immunotype strains and 19 differences in the gene from M982B L7 compared to MC58, and 12 differences in the M982B L7 sequence compared to that of 406Y L3. The gene from M982B L7 contains a frameshift mutation at nt. 454 and consequently would encode a truncated protein of only 151 amino acids.

The gene from *N. gonorrhoeae* F62 (SEQ. ID. NO: 3) shows 63 nt. differences compared to the *N. meningitidis* MC58, 62 nt. differences compared to the 406Y L3 gene and 66 compared to the M982B L7 gene. These differences in the DNA sequence of the *N. gonorrhoeae* F62 gene result in 16 or 17 amino acid differences in the protein, when compared to the MC58 L3 and 406Y L3 respectively.

Expression of the Sialyltransferase gene—Enzyme activity in *E. coli* carrying pNST plasmids could be easily detected and this expression of the lst gene depended on the vector derived lac promoter since there was no detectable enzyme activity when the gene's orientation was inverted. There was at least 30-fold more enzyme activity from the pNSTO-01 containing clones compared to *N. meningitidis* L3 strains. However the expression of the lst gene was not high enough to permit simple detection of an over-expressed protein by SDS-PAGE analysis. A plasmid was therefore constructed to introduce a c-myc immunodetection peptide tag at the C-terminal end of the protein. When this plasmid was used to express the lst gene, we could detect an immunoreactive protein with an M, 41,000, which is slightly shorter than the predicted size of the lst gene product. We also observed that the recombinant enzyme was mostly (76%) in the soluble fraction of the cell extracts, in contrast to the situation observed with the *N. meningitidis* extracts.

Acceptor Specificity of the lst Sialyltransferase—The natural acceptor for this enzyme is a terminal N-acetyllactosamine sequence on the lacto-N-neotetraose branch of the LOS from L3 immunotypes. We found that the enzyme would use as acceptors the synthetic saccharides: FCHASE-aminophenyl-LacNAc, FCHASE-aminophenyl-Lac, and FCHASE-aminophenyl-Gal, at 1:0.29:0.03 ratios of activity.

Discussion

The availability of a highly sensitive enzyme assay was instrumental in being able to screen for clones expressing the *N. meningitidis* α-2,3-sialyltransferase. The assay uses a glycosyltransferase acceptor which is easy to synthesize, and does not require specially constructed CE equipment as has been previously described for the ultra sensitive detection of glycosyltransferase reactions (Zhao, J. Y., et al. (1994) *Glycobiol.*, 4, 239–242). The acceptors used in this study were made from widely available glycosides, and fluorophores and the CE equipment used was commercially available. We were able to reliably detect attomole ($10^{-18}$ moles) quantities of reaction products which was more than adequate for screening for α-2,3-sialyltransferase expression.

The lst gene from MC58 L3 occurs between two genes unrelated to LOS synthesis, isocitrate dehydrogenase and cytochrome c', and is not part of a LOS synthesis operon unlike other *N. meningitidis* LOS glycosyltransferases (Jennings, M. P., et al. (1995) *Mol. Microbial.* 18, 729–740). This is similar to the situation with the *E. coli* and *N. meningitidis* α-2,8-polysialyltransferase involved in capsule biosynthesis, although these genes are adjacent to the CMP-Neu5Ac synthetase (Ganguli, S., et al. (1994) *J. Bacteriol.* 176, 4583–9). It is interesting to speculate that the lst gene is found on its own as the result of some kind of transposition event, although we have no evidence for insertion elements or transposon like sequences flanking the gene. Sequence analysis and database comparisons showed this gene to be distinct from both the mnammalian α-2,3-sialyltransferase family, and the bacterial α-2,8-sialyltransferase family, and the bacterial 3-deoxy-α-manno-octulosonic acid transferases which transfer a related sugar also from a CMP donor. The lst gene product was, however, shown to be similar to the lsg-02 gene product from *H. influenzae*. Although lsg-ORF2 has been demonstrated to be involved in LOS biosynthesis it may not encode an α-2,3-sialyltransferase since it was reported to be involved in the expression of a Gal-GlcNAc LOS epitope (McLaughlin, R., et al. (1992) *J. Bacteriol.* 174, 6455–6459). For the cloning of the *N. gonorrhoeae* gene the F62 strain was used as it has been have been shown to be common to both species (Jennings, M. P., et al. (1995) *Mol. Microbial.* 18, 729–740). An examination of the gene derived from *N. gonorrhoeae* F62 shows only a small number of differences, which is similar to other LOS biosynthesis gene comparisons from *N. meningitidis* and *N. gonorrhoeae* (Jennings, M. P., et al. (1995) *Mol. Microbial.* 18, 729–740).

The protein encoded by the lst gene appears to have an uncleavable signal peptide and computer aided prediction programs suggest that the sialyltransferase is an integral inner membrane protein. The original papers describing the sialyltransferase activity from both *N. meningitidis* and *N. gononrhoeae* suggest that the ST would be an outer membrane protein on the basis that the enzyme activity is extracted from whole cells by a Triton X-100 extraction (Mandrell, R. E., et al. (1993) *Microb. Pathog.* 14, 315–327; Mandrell, R. E., et al. (1993) *Microb. Pathog.* 14, 315–327). We have observed that the activity from *N. meningitidis* extracts shows association of the activity with the membrane fraction, but that in *E. coli* the activity appears to be mostly soluble.

That this gene functions in the sialylation of LOS is inferred from an examination of *N. meningitidis* M982B L7, which appears to be a natural sialyltransferase mutant. The sialyltransferase gene derived from this L7 strain contains a frame shift mutation at nt. 454 which renders it inactive in the recombinant plasmid carrying it, which agrees with our observation that sialyltransferase activity can not be detected in M982B cells. This strain produces the same lacto-N-neotetraose as the L3 strains do, but does not sialylate its LOS. The acceptor specificity for the L3 enzyme with synthetic acceptors shows a strong preference for N-acetyllactosamine over lactose or galactose. Also the product of the reaction using enzyme from *N. meningitidis* and FCHASE-LacNAc acceptor was unequivocally determined by NMR to be FCHASE-α-2,3-sialyl-acetyllactosamine.

The expression level of the recombinant gene is 50–100 U per liter of culture, based on assays with the FCHASE-LacNAc acceptor.

EXAMPLE 2

This example describes experiments further investigating the structure and specificity of the recombinant α-2,3-sialyltransferase from *Neisseria meningitidis*.

Experimental Procedure

Basic Recombinant DNA Methods—Plasmid DNA isolation, restriction enzyme digestions, purification of DNA fragments for cloning, ligations and transformations were performed as recommended by the enzyme supplier, or the manufacturer of the kit used for the particular procedure. PCR was performed with Pwo polymerase as described by the manufacturer (Boehringer Mannheim, Laval, Que.). Restriction and DNA modification enzymes were purchased from New England Biolabs Ltd., Mississauga, Ont.

Protein Analysis—Protein concentration was determined using the bicinchoninic acid protein assay kit from Pierce (Rockford, Ill.). SDS-PAGE and Western blotting analysis of proteins transferred to PVDF membranes was performed as previously described above except that the primary antibody was an anti-His$_6$ antibody from Invitrogen (San Diego, Calif.).

Expression Plasmid Construction—The complete *N. meningitidis* α-2,3-sialyltransferase gone as well as 0.57 kb of upstream sequence were amplified using the standard M13 "reverse" primer as the 3' primer and SIALM-17R (SEQ ID NO: 8) as the 5' primer (63-mer: 5'-CCTAGGTCGACTCATTA GTGGTGATGGTGGTGATGATTTTATCGTCAAATGT CAAAATC GGG-3'; the SalI site is shown in bold italics; the sequence encoding the His$_6$ tail is underlined) and pNST-01 as the template. The plasmid pNST-18 was constructed by digesting the PCR product with EcoRI and SalI and cloning it in a modified version of pCWori+(16), in which the laczα gene fragment has been deleted.

Production and Purification of the α-2,3-Sialyltransferase—A culture of *E. coli* BMH71-18/pNST-18 was used to inoculate a 1 L culture containing Luria broth medium (10 g tryptone, 5 g NaCl, and 10 g yeast extract per liter) with 150 mg/L ampicillin. The 1 L culture was grown overnight at 37° C. and used to inoculate 20 L of Terrific broth medium (16 g tryprone, 24 g yeast extract, 5 g NaCl, 10 mM potassium phosphate pH 7.4, and 0.8% glycerol per titer) containing 150 mg/L ampicillin. The 21 L culture was grown at 30° C. in a 28-L New Brunswick Scientific (Edison, N.J.) fermenter (model MF 128S) until $A_{500}$=0.55 and was then induced with 0.5 mM IPTG. The cells were collected after 17 hours, concentrated by ultrafiltration, washed with 0.85% NaCl and centrifuged. The cell paste (12 g wet weight) was resuspended in 60 mL of 20 mM Tris pH 8 and cell extracts were prepared using an Avestin C5 Emulsiflex cell disrupter (Avestin, Ottawa, Ont.). A protease inhibitor cocktail (Complete™ from Boehringer Mannheim) was added to the extract which was centrifuged twice at 20,000×g ($r_{max}$) for 30 min. The supernatant was centrifuged 1 h at 205,800×g ($r_{max}$) and the pellet was resuspended in 10 mM HEPES pH 7, 0.5 M NaCl and 0.2% Triton X-100. The resuspended pellet was stirred for 2 h at 4° C. and re-centriftiged 1 h at 205,800×g. The supernatant was applied to two 5-mL HiTrap Chelating column (Pharmacia Biotech) charged with $Ni^{2+}$, the maximum load being 25 mg total protein in each run. The columns were developed with a 60–800 mM imidazole gradient in 10 mM HEPES (pH 7) containing 0.5 M NaCl and 0.2% Triton X-100.

Primary Sequence Analysis of the α-2,3-Sialyltransferase—Purified α-2,3-sialyltransferase, 500 Lg, was dissolved in 6 M guanidinium-HCl, 100 mM Tris pH 8.3, reduced with DTT (5 equiv./mol of protein thiol) and S-arboxymethylated with iodoacetic acid (10 equiv./mol of protein thiol). The reaction mixture was then extensively dialysed against water. Automated gas-phase amino acid sequencing was performed on an Applied Biosystems (Foster City, Calif.) protein sequencing system incorporating a model 470A gas-phase sequencer equipped with an on-line model 120A PTH analyzer under the control of a model 900A control and data analysis module. For cleavage by CNBr, 100 μg of S-carboxymethylated α-2,3-sialyltransferase was dissolved in 500 μL of 88% (v/v) formic acid followed by the addition of 50 μg of CNBr. The reaction vial was flushed with argon, sealed and incubated in the dark for 24 h. For the digestion with trypsin, 100 μg of S-carboxymethylated α-2,3-sialyltransferase was dissolved in 50 mM ammonium bicarbonate, pH 8.0. Sequencing grade trypsin (Boehringer Mannheim) was added in a 1:100 (w/w) ratio, and mixture was incubated for 3 h at 37° C., after which the addition of trypsin and incubation were repeated. The freeze-dried tryptic and CNBr cleavage products were dissolved in 50 μL 0.1% trifluoroacetic acid and fractionated on a Synchropak 1 mm×10 cm RP-8 HPLC column (Keystone Scientific Inc., Bellefonte, Pa.) using a 0–90% acetonitrile gradient in 0.05% (v/v) trifluoroacetic acid. Mass analysis was performed by direct infusion of the HPLC effluent into a Fisons Instruments (Manchester, U.K.) VG electrospray Quattro triple quadrupole mass spectrometer with a mass range of 3500 amu/e.

Measurement of Sialyltransferase Activity and Survey of Oligosaccharide Acceptors—FCHASE-labelled oligosaccharides were prepared as described above, while the APTS-labelled oligosaccharides were prepared by reductive amination of reducing saccharides according to the method described by Guttman et al. (*Anal. Biochem* 233:234 (1996)) The Gal-β-APTS acceptor was derived from labelling of lactose; the Gal-α-APTS acceptor was derived from labelling of melibiose; the N-acetyllactosamine (LacNAc) acceptor was synthesized by APTS labelling of chieobiose, followed by enzymatic modification with bovine β-Galactosyl transferase to produce the LacNAc moiety-, the Gal-α-1,4-Gal-β acceptor was enzymatically synthesized from β-Gal-APTS with the α-1,4-galactosyltransferase from *N. meningitidis*. All of the reductive amination products were purified by gel permeation chromatography on Toyopearl HW40F (Sigma-Aldrich), 1.5 cm×15 cm column, using water as the eluant. It should be mentioned that all of these molecules have the terminal reducing sugar ring opened in the process of labelling. APTS-saccharides were quantitated by measuring the $A_{455}$, and using an extinction coefficient of 17160 $M^{-1}$ $cm^{-1}$. The TMR-labelled oligosaccharides were prepared as described by Zhao et al. (1994) *Glycobiology* 4:239–242. For the TMR labelled acceptors we used an extinction coefficient of 80,000 $M^{-1}$ $cm^{-1}$ for quantitation. The sialyltransferase activity was routinely measured using 0.5 mM FCHASE-N-acetyllactosamine as the acceptor and the assay conditions as described above. For measurement of $K_m$, and $k_{cat}$ values, assays were performed with the APTS labelled saccharides at room temperature. Assays were monitored so that for all acceptor concentrations, no more than 10% conversion to product occurred. The ranges of acceptor and donor concentrations were determined empirically, then a range spanning $0.2K_m$, up to $5K_m$, was used to obtain the values. Data were examined using the Grafit™ 3.0 software package (Erithacus Software, London, UK).

The reaction mixtures from the FCHASE- and APTS-labelled acceptors were analyzed by capillary electrophoresis performed with a Beckman instruments (Fullerton, Calif.) P/ACE 5510 equipped with a 3 mW Argon-ion laser induced fluorescence detector, $\lambda$ excitation=488 nm $\lambda$ emission=520 nm. The Capillary was of bare silica 75$\mu$×57 cm, with the detector at 50 cm. The capillary was conditioned before each run by washing with 0.2 M NaOH for 2 min., water for 2 min., and either 20 mM sodium phosphate buffer, pH 7.4 or sodium tetraborate, pH 9.3, 2 min. Samples were introduced by pressure injection for 2–5 seconds, and the separation was performed at 18 kV, 75 $\mu$A. Peak integration was performed with the Beckman PACE-Station software (version 1).

The reaction mixtures from the TMR-labelled acceptors were analyzed by thin layer chromatography on silica-60 TLC plates (Merck) using isopropanol/1-butanol/0.1 M HCL (2:1:1) as the solvent for development and a 365 nm UV lamp for the detection of the products.

Sialylation of FCHASE-thio-N-acetyllactosamine with N-acetyl-, N-propionyl and N-glycolyl-Neuraminic Acid—The 50 $\mu$L reaction mixtures included 0.8 MM acceptor, and 2 mM of either Neu5Ac, Neu5Gc or Neu5Pr, in 100 mM Tris pH 7.5. 0.2 mM DTT, 10 mM MgCl2, mM CTP, with 50 mU inorganic pyrophosphatase (Sigma). 47 mU CMP-Neu5Ac synthetase, 5 mU purified $\alpha$-2,3-sialyl-transferase. The reaction mixes were incubated at 32° C. for 90 min and product formation was followed by TLC analysis. The masses of the sialylated products were measured in the negative ion mode on a VG Quattro triple quadrupole mass spectrometer (Fisons Instruments).

Preparative Synthesis of Neu5Ac-$\alpha$-(2→3)-Gal-$\alpha$-(1→4)-Gal-$\beta$-FCHASE—A 1.2 ml reaction mixture composed of 1.48 mM FCHASE-Lac. 2.0 mM, UDP-Gal, in 50 mM HEPES pH 7.4, 10 mM $MnCl_2$, 5 mM DTT, and 3 U (1 mg) of $\alpha$-1,4-galactosyltransferase from *N. meningitidis* was incubated at room temperature for 80 min. at which time the reaction appeared complete by TLC (Wakarchuk, et al. (1996) *J. Biol. Chem.* 271:19166–19173). The reaction mixture was then diluted with water to 20 ml and desalted by SepPak C-18 reversed phase chromatography. The product was eluted in 50% acetonitrile, and evaporated to dryness. The $\alpha$-2,3-sialyl-transferase reaction was performed in 1 ml of 2.4 mM FCHASE-Lac-Gal, 5 mM CTP, 5 mM Neu5Ac, in 100 mM Tris-HCl, pH 7.5, 10 mM $MgCl_2$, 10 mM $MnCl_2$, 0.2 mM DTT and 0.1% Triton X-100, with 0.5 U $\alpha$-2,3-sialyltransferase (Triton X-100 extract of the *E. coli* membrane preparation), and 2.5 U of CMP-Neu5Ac synthetase. This reaction was performed at room temperature and allowed to proceed for 2 h. at which time the reaction was centrifuged to remove a precipitate, and another 0.5 U of $\alpha$-2,3-sialyltransferase was added and the reaction was left overnight. The product was again isolated by SepPak chromatography and purified by preparative TLC as previously described (Wakarchuk, W. W. et al. (1996) *J. Biol. Chem.* 271:19166–19173). The material was exchanged into $D_2O$ and examined by NMR spectroscopy for structural analysis.

NMR data was collected on a Bruler AMX 500 spectrometer using standard Bruker software as previously described (Wakarchuk, W. W. et al. (1996) *J. Biol. Chem.* 271:19166–19173). A portion of the NMR sample was used for methylation analysis. The lyophilized material was methylated with iodoinethane in dimethylsulfoxide containing an excess of potassium (methylsuccinyl) methanide as previously described (20), while the hydrolysis step employed 2M trifluoroacetic acid.

Results

Production and Purification of the $\alpha$-2,3-sialyltransferase'The *N. meningitidis* $\alpha$-2,3-sialyltransferase was overexpressed in *E. coli* using a construct (pNST-18) that included 0.57 kb of the original upstream sequence, the complete structural gene and a 5' sequence encoding a $His_6$ tail. Deletion of the 0.57 kb upstream sequence reduced the production of $\alpha$-2,3-sialyltransferase by at least 90% (data not shown) and consequently this sequence was included for overexpression although the reasons for its effect were not investigated. A 21-L culture of *E. coli* BMH71-18 gave a production of 750 U/L after 17 h of IPTG induction. When cell homogenates were fractionated by a sequence of 20,000×g and 205,800×g centrifugations, 45% of the $\alpha$-2,3-sialyltransferase activity was found in the 20,000×g pellet, 50% of the activity was found in the 205,800×g pellet and less than 5% of the activity was found in the 205,800×g supernatant. Analysis by SDS-PAGE (FIG. 1) followed by detection with an anti-$His_6$ antibody confirmed that the $\alpha$-2,3-sialyltransferase was associated with the membranes (205,800×g pellet) rather than with the soluble fraction of the extract (205,800×g supernatant).

Using buffers containing 0.2% Triton X-100, we could extract 60–70% of the activity associated with the membranes. SDS-PAGE analysis followed by scanning densitometry of the Coomassie stained gel indicated that the $\alpha$-2,3-sialyl-transferase represented 35% of the total protein present in the Triton X-100 extract (FIG. 1). From this we calculated the total amount of $\alpha$-2,3-sialyltransferase in the extract from 1 L of culture was ~250 mg. The Triton X-100 extract was applied to an IMAC column and the $\alpha$-2,3-sialyltransferase eluted in the fractions containing between 400 and 550 mM imidazole. The purified $\alpha$-2,3-sialyltransferase had a specific activity of 1.44 U/mg and the overall purification yield was 1.1% (Table 1).

SDS-PAGE analysis of the purified $\alpha$-2,3-sialyltransferase showed two bands with apparent molecular mass of 41 kDa and 83 kDa, respectively. Since the deduced amino acid sequence predicts a mass of 43.4 kDa, the 41 kDa band is presumed to be a monomeric form of the $\alpha$-2,3-sialyltransferase while the 83 kDa form would be a dimeric form. Scanning densitometry of the gel indicated that the monomeric form and the dimeric form represented 90% and 10%, respectively, of the total purified protein. Both bands were detected by the anti-$His_6$ antibody and they were both active when corresponding unstained portions of the gel were cut out and renatured in buffer containing 0.2% Triton X-100 and 0.2 mM DTT. In some of the preparations there was also a light band of high molecular mass material that barely entered the gel and that also reacted with the anti-$His_6$antibody.

Primary Sequence Analysis of the Purified $\alpha$-2,3-Sialyltransferase—The observed sequence was in agreement with the deduced amino acid sequence (SEQ. ID. NO:2, GenBank U60660). The amino acid, sequencing also indicated that most of he recombinant $\alpha$-2,3-sialyltransferase had a processed N-terminus as the major sequence started with the second residue (Gly) while a less abundant (but distinct) sequence started with the N-terminal Met residue.

The reduced and S-carboxymethylated α-2,3-sialyltransferase was also cleaved using CNBr (cleavage of peptide bonds adjacent to Met) and trypsin (cleavage of peptide bonds adjacent to Lys and Arg). The peptides were analyzed by LC-ESI-MS and the observed masses were compared with the masses from in a computer-generated list of all the possible peptides obtained by either CNBr or trypsin cleavage. The observed peptides accounted for 95% of the deduced amino acid sequence and included N-terminal and C-terminal peptides (CB3 and CB14).

Figure 2:
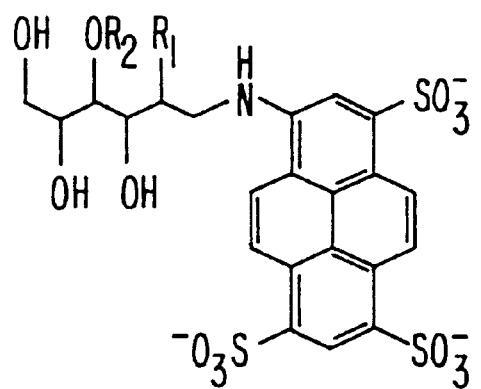
FIGS. 2A and 2B show structures of the flugrophores used in the capillary electrophoresis assay of the α-2,3- sialyltransferase.
Figure 2:
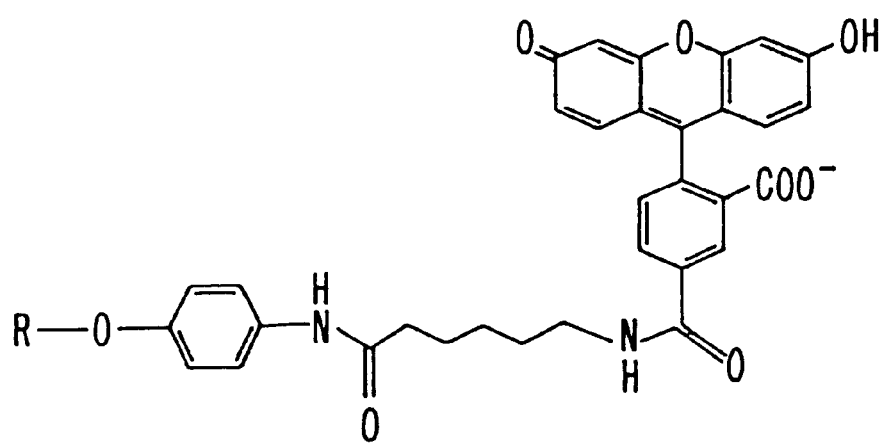

Enzymatic properties—Using either FCHASE-LacNAc or the APTS labelled acceptors (FIG. 2), we observed an optimal pH of 6 for the purified α-2,3-sialyltransferase. The activity was simulated 3-fold by the presence of 20 mM $MgCl_2$ and 4-fold by the presence of 20 mM $MnCl_2$, although these metals were not essential factors since the enzyme was still active in the presence of 5 mM EDTA. Although $MnCl_2$ provided the best stimulatory effect in a short-term assay (5 min), the α-2,3-sialyltransferase precipitated in its presence during long-term (>30 min) incubations. Consequently $MgCl_2$ was preferred for preparative syntheses. DTT had no effect on the activity when assayed in the 1–20 mM range. The nucleotides CMP and CDP were inhibitory, a concentration of 1 mM CMP produced 80% inhibition in a standard assay, and CDP produced 40% inhibition at the same concentration.

Sialylation of FCHASE-N-acetyllactosamine with N-acetyl, N-propionyl and N-glycolyneuraminic acid—The ability of the α-2,3-sialyltransferase to use donors other than CMP-Neu5Ac was tested using coupled reactions with the N. meningitidis CMP-Neu5Ac synthetase to activate Neu5Gc or Neu5Pr in the presence of CTP. A control reaction with Neu5Ac yielded complete conversion of the acceptor (FCHASE-LacNAc) in 60 min while the reaction with Neu5Pr took 90 min to reach completion. The reaction with Neu5Gc reached above 90% conversion after 120 min of incubation. The products were analyzed by mass spectrometry and the observed masses were within 0.1% of the expected masses, confirming that in each case the acceptor had been sialylated with the expected sialic acid analog (Neu5Ac, Neu5Gc or Neu5Pr).

Survey of Oligosaccharides Acceptors for the α-2,3-sialyltransferase—The acceptor specificity of the α-2,3-sialyltransferase was first studied qualitatively using various fluorophore-labelled oligosaccharides that contained a terminal Gal residue (Table II). The survey of FCHASE-labelled oligosaccharides indicated that the α-2,3-sialyltransferase can use both α- and β-linked Gal as acceptor. The Gal could be a monosaccharide glycoconjugate but the enzyme will also use the Gal-α when it is linked to Gal-β(1→4)-Glc-β as in the P$^k$ antigen and the Gal-β when it is linked to either Glc or GlcNAc.

That the sialic acid was α-(2→3) to the Gal-α when FCHASE-P$^k$ was used as the acceptor was confirmed by methylation analysis and from a detailed assignment of the NMR spectra of the product from a preparative synthesis of this compound. Acid hydrolysis of a permethylated sample of sialylated product afforded approximately equal molar amount of 2,4,6-tri-O-methyl-Gal:2,3,6-tri-O-methyl-Gal and 2,3,6-tri-O-methyl-Glc. This indicated the oligosaccharide moiety contained 3-linked Gal, 4-linked Gal and 4-linked Glc residues. Complete assignment of the NMR spectra of the sialylated product was achieved by $^1$H-$^1$H and $^1$H-$^{13}$C chemical shift Correlation experiments (Table III). The chemical shift data is consistent with the proposed structure (Masoud, H. et al. (1997) Biochemistry 36:2091–2103; the down field shifted values for the Gal-α C-3 and H-3 resonances compared to the unsubstituted analogues [$^1$H: ca. 0.2 ppm, $^{13}$C: ca. 2.8 ppm, (Masoud, H. et al. (1997) Biochemistry 36:2091–2103)] being indicative of the Neu5Ac-α-(2→3)-Gal-α linkage which was further indicated from occurrence of an NOE between H-3 protons of the NeuSAc, and Gal-α residues.

The survey of the TMR-labelled oligosaccharides showed that the α-2,3-sialyltransferase can use a terminal Gal that is either β-(1→3) or β-(1→4) linked to GlcNAc as long as the GlcNAc is not substituted with fucose (e.g. Lewis-X). The α-2,3-sialyltransferase also tolerated sulfur as the linkage atom as we observed product formation with Gal-β-thio-FCHASE and Gal-β-(1→4)-GlcNAc-β-thio-FCHASE.

Determination of kinetic constants—We found an apparent $K_m$ of 20 $\mu$M for the donor CMP-Neu5Ac using as the acceptor either LacNAc-APTS (at 0.8 mM) or lacto-N-neotetraose-APTS (at 0.2 mM). No significant substrate inhibition was observed when the enzyme was assayed with as high as 1 mM CMP-Neu5Ac. Using a CMP-Neu5Ac concentration of 200 $\mu$M, we determined the kinetic constants for several APTS-labelled oligosaccharides (Table IV). The α-2,3-sialyltransferase showed comparable activity toward the two monosaccharide acceptors (α- and β-linked Gal). A 5.5 fold decrease in apparent $K_{cat}/K_m$ was observed when the terminal Gal was α-(1→4) linked to Gal-β-(1→4)-Glc-β. On the other hand the apparent $K_{cat}/K_m$ toward the terminal Gal-β increased 5 fold when was β-(1→4) linked to GlcNAc (LacNAc) and 10 fold when the acceptor was lacto-N-neotetraose. However the apparent $K_{cat}/K_m$ with the β-(1→3) linked Gal in lacto-N-tetraose was comparable to the monosaccharide acceptors and consequently was 10 fold lower than with the β-(1→4) linked Gal in lacto-N-neotetraose.

Discussion

Examinations of the acceptor specificity of several mammalian α-2,3-sialyltransferases have shown that they are specific for the terminal sugar, the sugar next to the terminal Gal, and the linkage between these two sugars (Kitagawa, H. et al. (1993) Biochem. Biophys. Res. Commun. 194:375–382). We determined the affinity of the bacterial enzyme for several acceptors to compare its properties with those of its mammalian equivalents, and to evaluate its suitability for use in chemi-enzymatic synthesis. Enzymatic kinetic parameters were measured with APTS-labelled saccharides which had the advantage of being more soluble than FCHASE-labelled saccharides and were still suitable for ultra-sensitive assay using capillary electrophoresis and laser-induced fluorescence detection. We observed that the bacterial enzyme was influenced by linkages to the penultimate sugar, but that it would modify a terminal Gal which was α-linked either to Gal or an aglycone. The turnover number and specificity constant for such acceptors (Table IV) shows that they are used reasonably well.

The apparent $K_m$ and $k_{cat}$ values from the other acceptors indicated that the α-2,3-sialyltransferase had activity consistent with which oligosaccharides are presented as acceptors in the parent L3 immunotype LOS. So, as would be predicted, lacto-N-neotetraose showed the highest $k_{cat}/K_m$ while the disaccharide LacNAc was almost as specific. The α-2,3-sialyltransferase can also accommodate lacto-N-tetraose but as the terminal Gal is β-(1→3) linked the activity is 10-fold lower than with lacto-N-neotetraose. Mammalian α-2,3-sialyltransferases are also able to use both β-(1→3) and β-(1→4) linked Gal, but some have a preference for Gal-β-(1→3) while others have a preference for Gal-β-(1→4) and a ratio of activities similar to that observed with the bacterial enzyme (Kitagawa, H. et al. (1994) *J. Biol. Chem.* 269: 1394–1401).

It has been shown that some mammalian sialyltransferases can use different analogs of sialic acid donors and this property can be used to synthesize sialylated oligosaccharides with modified biological activity (Higa, H. H. et al. (1985) *J. Biol. Chem.* 260:8838–8849; Zou, W. et al. (1996) *Carbohydr. Res.* 296:209–228). Using coupled reactions with the *N. meningitidis* CMP-Neu5Ac synthetase, we found that the *N. meningitidis* α-2,3-sialyltransferase could use alternate donors such as Neu5Pr and Neu5Gc although at rates lower than with Neu5Ac.

The qualitative survey of acceptor oligosaccharides showed that *N. meningitidis* α-2,3-sialyltransferase will tolerate sulfur as the linkage atom both in the case of a monosaccharide (β-Gal-thio-FCHASE) and a disaccharide (Gal-β-(1→4)-GlcNAc-β-thio-FCHASE) acceptors. This property will be useful to synthesize activated oligosaccharides to be used as donors in chemical syntheses (Rademann, J. et al. (1996), *Tetrahedron Lett.* 37:3989–3990).

The purified α-2,3-sialyltransferase required the presence of Triton X-100 to remain in solution and had a tendency to precipitate when concentrated above 1 mg/ml (1 to 2 U/mL) by ultrafiltration. Attempts to separate the dimeric form from the monomeric form by gel filtration failed since both forms eluted in a single very wide peak while the overall yield was very low. It is known that purified α-2,3-sialyltransferase tends to form aggregates and can easily be lost through non-specific adsorption even in the presence of detergent. In fact, the α-2,3-sialyltransferase from Neiseria has never been purified from a natural source and the low purification yield obtained from an overexpressing system suggests why purifying this enzyme from a wild-type source has been very difficult. The exact localization (inner or outer membrane) has not been determined experimentally but there is no doubt that the α-2,3-sialyltransferase is associated with membranes, both in Neisseria and when it is overexpressed in *E. coli*.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

TABLE I

Summary of the purification of the α-2,3-sialyltransferase Example of the yield and specific activity obtained when the α-2,3-sialyltransferase was purifid from 0.6 L of culture of *E. coli* carrying pNST-18.

| Step | Volume (mL) | Protein (mg) | Total activity (U) | Specific activity (U/mg) | Yield (%) | Purification (fold) |
|---|---|---|---|---|---|---|
| Crude extract | 72 | 2376 | 444.1 | 0.19 | 100 | 1 |
| 205,800 g pellet | 32 | 291.2 | 243.0 | 0.83 | 55 | 4.5 |
| TX-100 extract | 186 | 180.4 | 171.8 | 0.95 | 39 | 5.1 |
| IMAC | 18 | 4 | 4.9 | 1.44 | 1.1 | 7.7 |

TABLE II

Acceptor specificity of the purified recombinant α-2,3-sialyltransferase

| Acceptor | Linkage Atom | Aglycone | Concentration (mM) | Product detected (+/−) |
|---|---|---|---|---|
| Gal-β | S | AH-FCHASE[a] | 1.0 | + |
| Gal-β | O | AP-FCHASE[b] | 0.5 | + |
| Gal-β-(1-4)-GlcNAc-β | O | AP-FCHASE | 0.5 | + |
| Gal-β-(1-4)-GlcNAc-β | S | AH-FCHASE | 0.8 | + |
| Gal-β-(1-4)-Gle-β | O | AP-FCHASE | 0.5 | + |
| Gal-α | O | AP-FCHASE | 0.5 | + |
| Gal-α-(1-4)-Gal-β-(1-4)-β-Glc-β | O | AP-FCHASE | 0.5 | + |
| Gal-β-(1-4)-GlcNAc-β | O | TMR[c] | 0.5 | + |
| Gal-β-(1-3)-GlcNAc-β | O | TMR | 0.5 | + |
| Gal-β-(1-4)-[Fuc-α-(1-3)]-GlcNAc-β | O | TMR | 0.5 | − |
| Gal-β-(1-4)-[Fuc-α-(1-3)]-GlcNAc-β | O | TMR | 0.25 | − |

[a]aminohexylthio linker to FCHASE
[b]aminophenyl linker to FCHASE
[c]hydrazinocarbonyloctyl (Lemieux) linker to TMR

TABLE III $^1$H and $^{13}$C NMR chemical Shifts[a] for the oligosaccharide moiety of Neu5 Ac-α-(2-3)-Gal-α-(1-4)-Gal-β-(1-4)-Glc-β-FCHASE

| | Sugar Residue | | | | | | | |
|---|---|---|---|---|---|---|---|---|
| | Neu5Ac | | Gal-α | | Gal-β | | Glc-β | |
| Position | H | C | H | C | H | C | H | C |
| 1 | — | — | 5.01 | 101.0 | 4.41 | 104.6 | 4.81 | 100.5 |
| 2 | — | — | 3.91 | 67.7 | 3.61 | 72.0 | 3.31 | 73.6 |
| 3$_{ex}$ | 1.83 | 40.7 | 4.41 | 72.8 | 3.76 | 73.0 | 3.61 | 75.3 |
| 3$_{eq}$ | 2.77 | | — | | — | | — | |
| 4 | 3.70 | 69.3 | 4.11 | 68.8 | 4.10 | 77.6 | 3.45 | 80.2 |
| 5 | 3.85 | 52.4 | 4.39 | 71.8 | 3.87 | 76.3 | 3.54 | 80.2 |
| 6 | 3.62 | 73.6 | 3.70 | 61.6 | 3.88 | 61.1 | 3.40 | 60.8 |
| 6' | — | 3.70 | | 3.98 | | 3.86 | | |
| 7 | 3.61 | 69.0 | | | | | | |
| 8 | 3.92 | 72.5 | | | | | | |
| 9 | 3.70 | 63.5 | | | | | | |
| 9' | 3.92 | | | | | | | |
| NAc | 2.13 | 24.9 | | | | | | |

[a]First order chemical shifts measured at 37° C. in D$_2$O are referenced to the methyl resonance of acetone (2.225 ppm for $^1$H and 31.07 ppm for $^{13}$C). For each sugar residue the $^1$H data is recorded in the lefthand column and the $^{13}$C data is on the right column. Within experimental error, the chemical shift data for the aminophenyl-(6-5-(fluoresceincarboxamido)-hexanoic acid amide) moiety are the same as those previously reported (9).

TABLE IV

K$_m$ k$_{cat}$ values for APTS-labelled acceptors of the purified recombinant α-2-3-sialyltransferase

| Acceptor | K$_m$ (μM) | k$_{cat}$ (min$^{-1}$) | k$_{cat}$[K$_m$ (min$_{-1}$ × mM$_{-1}$) |
|---|---|---|---|
| Gal-□-(1-4)-GlcNAc-β-(1-3)-Gal-β-(1-4)-Glc* (lacto-N-neotetraose) | 42 (±5.7) | 9.5 | 228 |
| Gal-β-(1-4)-β-GlcNAc-β-GlcNAc* (LacNAc) | 67 (±7.1) | 7.1 | 105 |

TABLE IV-continued $K_m$ $k_{cat}$ values for APTS-labelled acceptors of the purified recombinant α-2-3-sialyltransferase

| Acceptor | $K_m$ (μM) | $k_{cat}$ (min$^{-1}$) | $k_{cat}/K_m$ (min$_{-1}$ × mM$_{-1}$) |
|---|---|---|---|
| Gal-α-(1-6)-Gal* | 221 (±20) | 6.8 | 31 |
| Gal-β-(1-4)-Glc* | 168 | 3.8 | 22 |
| Gal-β-(1-3)-GlcNAc-β-(1-3)-Gal-β-(1-4)-Glc* (lacto-N-tetraose) | 113 (±9.0) | 2.3 | 20 |
| Gal-α-(1-4)-Gal-(1-4)-β-Glc* (P$^k$) | 139 (±12) | 0.8 | 5.6 |

*This sugar is the site of reductive amination with APTS and thus the ring is open.

What is claimed is:

1. An isolated α2,3-sialyltransferase polypeptide having a sequence at least 80% identical to SEQ. ID. NO: 2.

2. The α2,3-sialyltransferase polypeptide of claim 1 which has a molecular weight of about 40 kD.

3. The α2,3-sialyltransferase polypeptide of claim 1 which has a sequence as shown in SEQ. ID. NO: 2.

4. An isolated α2,3-sialyltransferase polypeptide having a sequence at least 80% identical to SEQ ID NO: 4.

5. The α2,3-sialyltransferase polypeptide of claim 4 which has a molecular weight of about 40 kD.

6. The α2,3-sialyltransferase polypeptide of claim 4 which has a sequence as shown in SEQ. ID. NO: 4.

7. A method of adding a sialic acid residue to an acceptor molecule comprising a terminal galactose residue, the method comprising contacting the acceptor molecule with an activated sialic acid molecule and an α2,3-sialyltransferase having a sequence at least 80% identical to SEQ. ID. NO: 2 or SEQ. ID. NO: 4.

8. The method of claim 7, wherein the terminal galactose residue is linked through an α linkage to a second residue in the acceptor molecule.

9. The method of claim 7, wherein the terminal galactose residue is linked through a β linkage to a second residue in the acceptor molecule.

10. The method of claim 9, wherein the linkage is a β1,4 linkage.

11. The method of claim 9, wherein the linkage is a β1,3 linkage.

12. The method of claim 7, wherein the activated sialic acid is CMP-Neu5Ac.

\* \* \* \* \*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1116 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Neisseria meningitidis
      (B) STRAIN: 406Y, NRCC 4030
      (C) INDIVIDUAL ISOLATE: Capsule type: Y; lipooligosaccharide type: L3

(ix) FEATURE:
      (A) NAME/KEY: CDS
      (B) LOCATION: 1..1116
      (D) OTHER INFORMATION: /product= "alpha-2,3-sialyltransferase"

(xi) SEQUENCE DESCRIPTION: SEQ ID NO:1:

```
ATG GGC TTG AAA AAG GCT TGT TTG ACC GTG TTG TGT TTG ATT GTT TTT        48
Met Gly Leu Lys Lys Ala Cys Leu Thr Val Leu Cys Leu Ile Val Phe
 1               5                  10                  15

TGT TTC GGG ATA TTT TAT ACA TTT GAC CGG GTA AAT CAT GGG GAA AGG        96
Cys Phe Gly Ile Phe Tyr Thr Phe Asp Arg Val Asn His Gly Glu Arg
            20                  25                  30

AAT GCG GTT TCC CTG CTG AAG GAC AAA CTC TTC AAT GAA GAG GGG GAA       144
Asn Ala Val Ser Leu Leu Lys Asp Lys Leu Phe Asn Glu Glu Gly Glu
        35                  40                  45

CCG GTC AAT CTG ATT TTC TGC TAT ACC ATA TTG CAG ATG AAG GTG GCG       192
Pro Val Asn Leu Ile Phe Cys Tyr Thr Ile Leu Gln Met Lys Val Ala
    50                  55                  60

GAA AGG ATT ATG GCG CAG CAT CCG GGG GAG CGG TTT TAT GTG GTG CTG       240
Glu Arg Ile Met Ala Gln His Pro Gly Glu Arg Phe Tyr Val Val Leu
65                  70                  75                  80

ATG TCT GAA AAC AGG AAT GAA AAA TAC GAT TAT TAT TTC AAG CAG ATA       288
Met Ser Glu Asn Arg Asn Glu Lys Tyr Asp Tyr Tyr Phe Lys Gln Ile
                85                  90                  95
```

```
AAG GAT AAG GCG GAG CGG GCG TAT TTT TTC CAC CTG CCC TAC GGT TTG      336
Lys Asp Lys Ala Glu Arg Ala Tyr Phe Phe His Leu Pro Tyr Gly Leu
            100                 105                 110

AAC AAA TCG TTT AAT TTC ATT CCG ACG ATG GCG GAG CTG AAG GTA AAG      384
Asn Lys Ser Phe Asn Phe Ile Pro Thr Met Ala Glu Leu Lys Val Lys
                115                 120                 125

TCG ATG CTG CTG CCG AAA GTC AAG CGG ATT TAT TTG GCA AGT TTG GAA      432
Ser Met Leu Leu Pro Lys Val Lys Arg Ile Tyr Leu Ala Ser Leu Glu
130                 135                 140

AAA GTC AGC ATT GCC GCC TTT TTG AGC ACT TAC CCG GAT GCG GAA ATC      480
Lys Val Ser Ile Ala Ala Phe Leu Ser Thr Tyr Pro Asp Ala Glu Ile
145                 150                 155                 160

AAA ACC TTT GAC GAC GGG ACA GGC AAT TTA ATT CAA AGC AGC AGC TAT      528
Lys Thr Phe Asp Asp Gly Thr Gly Asn Leu Ile Gln Ser Ser Ser Tyr
                165                 170                 175

TTG GGC GAT GAG TTT TCT GTA AAC GGG ACG ATC AAG CGG AAT TTT GCC      576
Leu Gly Asp Glu Phe Ser Val Asn Gly Thr Ile Lys Arg Asn Phe Ala
            180                 185                 190

CGG ATG ATG ATC GGA GAT TGG AGC ATC GCC AAA ACC CGT AAT GCT TCC      624
Arg Met Met Ile Gly Asp Trp Ser Ile Ala Lys Thr Arg Asn Ala Ser
        195                 200                 205

GAC GAG CAT TAC ACG ATA TTC AAG GGT TTG AAA AAC ATT ATG GAC GAC      672
Asp Glu His Tyr Thr Ile Phe Lys Gly Leu Lys Asn Ile Met Asp Asp
    210                 215                 220

GGC CGC CGC AAG ATG ACT TAC CTG CCG CTG TTC GAT GCG TCC GAA CTG      720
Gly Arg Arg Lys Met Thr Tyr Leu Pro Leu Phe Asp Ala Ser Glu Leu
225                 230                 235                 240

AAG GCG GGG GAC GAA ACG GGC GGC ACG GTG CGG ATA CTT TTG GGT TCG      768
Lys Ala Gly Asp Glu Thr Gly Gly Thr Val Arg Ile Leu Leu Gly Ser
                245                 250                 255

CCC GAC AAG GAG ATG AAG GAA ATT TCG GAA AAG GCG GCA AAA AAC TTC      816
Pro Asp Lys Glu Met Lys Glu Ile Ser Glu Lys Ala Ala Lys Asn Phe
            260                 265                 270

AAC ATA CAA TAT GTC GCA CCG CAC CCC CGC CAA ACC TAC GGG CTT TCC      864
Asn Ile Gln Tyr Val Ala Pro His Pro Arg Gln Thr Tyr Gly Leu Ser
        275                 280                 285

GGC GTA ACC ACA TTA AAT TCG CCC TAT GTC ATC GAA GAC TAT ATT TTG      912
Gly Val Thr Thr Leu Asn Ser Pro Tyr Val Ile Glu Asp Tyr Ile Leu
    290                 295                 300

CGC GAG ATT AAG AAA AAC CCG CAT ACG AGG TAT GAA ATT TAT ACC TTT      960
Arg Glu Ile Lys Lys Asn Pro His Thr Arg Tyr Glu Ile Tyr Thr Phe
305                 310                 315                 320

TTC AGC GGC GCG GCG TTG ACG ATG AAG GAT TTT CCC AAT GTG CAC GTT     1008
Phe Ser Gly Ala Ala Leu Thr Met Lys Asp Phe Pro Asn Val His Val
                325                 330                 335

TAC GCA TTG AAA CCG GCT TCC CTT CCG GAA GAT TAT TGG CTC AAG CCG     1056
Tyr Ala Leu Lys Pro Ala Ser Leu Pro Glu Asp Tyr Trp Leu Lys Pro
            340                 345                 350

GTG TAT GCC CTG TTT ACC CAA TCC GGC ATC CCG ATT TTG ACA TTT GAC     1104
Val Tyr Ala Leu Phe Thr Gln Ser Gly Ile Pro Ile Leu Thr Phe Asp
        355                 360                 365

GAT AAA AAT TAA                                                     1116
Asp Lys Asn
    370
```

(2) INFORMATION FOR SEQ ID NO:2:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO:2:

| Met | Gly | Leu | Lys | Lys | Ala | Cys | Leu | Thr | Val | Leu | Cys | Leu | Ile | Val | Phe |
|---|---|---|---|---|---|---|---|---|---|---|---|---|---|---|---|
| 1 | | | | 5 | | | | | 10 | | | | | 15 | |

Cys Phe Gly Ile Phe Tyr Thr Phe Asp Arg Val Asn His Gly Glu Arg
                    20                  25                  30

Asn Ala Val Ser Leu Leu Lys Asp Lys Leu Phe Asn Glu Glu Gly Glu
                35                  40                  45

Pro Val Asn Leu Ile Phe Cys Tyr Thr Ile Leu Gln Met Lys Val Ala
        50                  55                  60

Glu Arg Ile Met Ala Gln His Pro Gly Glu Arg Phe Tyr Val Val Leu
65                  70                  75                  80

Met Ser Glu Asn Arg Asn Glu Lys Tyr Asp Tyr Tyr Phe Lys Gln Ile
                85                  90                  95

Lys Asp Lys Ala Glu Arg Ala Tyr Phe Phe His Leu Pro Tyr Gly Leu
                100                 105                 110

Asn Lys Ser Phe Asn Phe Ile Pro Thr Met Ala Glu Leu Lys Val Lys
            115                 120                 125

Ser Met Leu Leu Pro Lys Val Lys Arg Ile Tyr Leu Ala Ser Leu Glu
130                 135                 140

Lys Val Ser Ile Ala Ala Phe Leu Ser Thr Tyr Pro Asp Ala Glu Ile
145                 150                 155                 160

Lys Thr Phe Asp Asp Gly Thr Gly Asn Leu Ile Gln Ser Ser Ser Tyr
                165                 170                 175

Leu Gly Asp Glu Phe Ser Val Asn Gly Thr Ile Lys Arg Asn Phe Ala
            180                 185                 190

Arg Met Met Ile Gly Asp Trp Ser Ile Ala Lys Thr Arg Asn Ala Ser
            195                 200                 205

Asp Glu His Tyr Thr Ile Phe Lys Gly Leu Lys Asn Ile Met Asp Asp
        210                 215                 220

Gly Arg Arg Lys Met Thr Tyr Leu Pro Leu Phe Asp Ala Ser Glu Leu
225                 230                 235                 240

Lys Ala Gly Asp Glu Thr Gly Gly Thr Val Arg Ile Leu Leu Gly Ser
                245                 250                 255

Pro Asp Lys Glu Met Lys Glu Ile Ser Glu Lys Ala Ala Lys Asn Phe
            260                 265                 270

Asn Ile Gln Tyr Val Ala Pro His Pro Arg Gln Thr Tyr Gly Leu Ser
            275                 280                 285

Gly Val Thr Thr Leu Asn Ser Pro Tyr Val Ile Glu Asp Tyr Ile Leu
        290                 295                 300

Arg Glu Ile Lys Lys Asn Pro His Thr Arg Tyr Glu Ile Tyr Thr Phe
305                 310                 315                 320

Phe Ser Gly Ala Ala Leu Thr Met Lys Asp Phe Pro Asn Val His Val
                325                 330                 335

Tyr Ala Leu Lys Pro Ala Ser Leu Pro Glu Asp Tyr Trp Leu Lys Pro
                340                 345                 350

Val Tyr Ala Leu Phe Thr Gln Ser Gly Ile Pro Ile Leu Thr Phe Asp
            355                 360                 365

Asp Lys Asn
370

(2) INFORMATION FOR SEQ ID NO:3:

(i) SEQUENCE CHARACTERISTICS:
    (A) LENGTH: 1116 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Neisseria gonorrhoeae
    (B) STRAIN: F62

(ix) FEATURE:
    (A) NAME/KEY: CDS
    (B) LOCATION: 1..1116
    (D) OTHER INFORMATION: /product= "alpha-2,3-sialyltransferase"

(xi) SEQUENCE DESCRIPTION: SEQ ID NO:3:

```
ATG GGG TTG AAA AAA GTC TGT TTG ACC GTG TTG TGC CTG ATT GTT TTT        48
Met Gly Leu Lys Lys Val Cys Leu Thr Val Leu Cys Leu Ile Val Phe
 1               5                  10                  15

TGC TTC GGG ATA TTT TAT ACG TTT GAC CGG GTA AAT CAG GGG GAA AGG        96
Cys Phe Gly Ile Phe Tyr Thr Phe Asp Arg Val Asn Gln Gly Glu Arg
                20                  25                  30

AAC GCG GTT TCC CTG CTG AAG GAC AAA CTC TTC AAT GAA GAG GGG AAA       144
Asn Ala Val Ser Leu Leu Lys Asp Lys Leu Phe Asn Glu Glu Gly Lys
            35                  40                  45

CCC GTC AAT CTG ATT TTC TGC TAT ACC ATA TTG CAG ATG AAG GTG GCA       192
Pro Val Asn Leu Ile Phe Cys Tyr Thr Ile Leu Gln Met Lys Val Ala
50                  55                  60

GAA AGG ATT ATG GCG CAG CAT CCG GGG GAG CGG TTT TAT GTG GTG CTG       240
Glu Arg Ile Met Ala Gln His Pro Gly Glu Arg Phe Tyr Val Val Leu
65                  70                  75                  80

ATG TCT GAA AAC AGG AAT GAA AAA TAC GAT TAT TAT TTC AAT CAG ATA       288
Met Ser Glu Asn Arg Asn Glu Lys Tyr Asp Tyr Tyr Phe Asn Gln Ile
                85                  90                  95

AAG GAT AAG GCG GAG CGG GCG TAT TTT TTC TAC CTG CCC TAC GGT TTG       336
Lys Asp Lys Ala Glu Arg Ala Tyr Phe Phe Tyr Leu Pro Tyr Gly Leu
            100                 105                 110

AAC AAA TCG TTT AAT TTC ATT CCG ACG ATG GCG GAG CTG AAG GTG AAG       384
Asn Lys Ser Phe Asn Phe Ile Pro Thr Met Ala Glu Leu Lys Val Lys
        115                 120                 125

TCG ATG CTG CTG CCG AAG GTC AAG CGG ATT TAT TTG GCG AGT TTG GAA       432
Ser Met Leu Leu Pro Lys Val Lys Arg Ile Tyr Leu Ala Ser Leu Glu
130                 135                 140

AAA GTC AGT ATT GCC GCC TTT TTG AGC ACT TAC CCG GAT GCG GAA ATC       480
Lys Val Ser Ile Ala Ala Phe Leu Ser Thr Tyr Pro Asp Ala Glu Ile
145                 150                 155                 160

AAA ACC TTT GAC GAC GGC ACA AAC AAC CTG ATA CGG GAG AGC AGC TAT       528
Lys Thr Phe Asp Asp Gly Thr Asn Asn Leu Ile Arg Glu Ser Ser Tyr
                165                 170                 175

TTG GGC GGC GAG TTT GCC GTA AAC GGG GCG ATT AAG CGG AAT TTT GCC       576
Leu Gly Gly Glu Phe Ala Val Asn Gly Ala Ile Lys Arg Asn Phe Ala
            180                 185                 190

CGA ATG ATG GTC GGG GAT TGG AGC ATC GCC AAA ACC CGC AAT GCT TCC       624
Arg Met Met Val Gly Asp Trp Ser Ile Ala Lys Thr Arg Asn Ala Ser
        195                 200                 205

GAC GAG CAT TAC ACG ATA TTC AAG GGT TTG AAA AAC ATT ATG GAT GAC       672
Asp Glu His Tyr Thr Ile Phe Lys Gly Leu Lys Asn Ile Met Asp Asp
210                 215                 220

GGC CGC CGC AAG ATG ACT TAC CTG CCG CTG TTC GAT GCG TCC GAA CTG       720
Gly Arg Arg Lys Met Thr Tyr Leu Pro Leu Phe Asp Ala Ser Glu Leu
225                 230                 235                 240
```

| | | | | | | | | | | | | | | | |
|---|---|---|---|---|---|---|---|---|---|---|---|---|---|---|---|
| AAG | GCG | GGG | GAC | GAA | ACG | GGC | GGC | ACG | GTG | CGG | ATA | CTT | TTG | GGT | TCG | 768
| Lys | Ala | Gly | Asp | Glu | Thr | Gly | Gly | Thr | Val | Arg | Ile | Leu | Leu | Gly | Ser |
| | | | 245 | | | | 250 | | | | | | 255 | | |

```
AAG GCG GGG GAC GAA ACG GGC GGC ACG GTG CGG ATA CTT TTG GGT TCG     768
Lys Ala Gly Asp Glu Thr Gly Gly Thr Val Arg Ile Leu Leu Gly Ser
            245             250                     255

CCC GAC AAA GAG ATG AAG GAA ATT TCG GAA AAG GCG GCA AAA AAT TTC     816
Pro Asp Lys Glu Met Lys Glu Ile Ser Glu Lys Ala Ala Lys Asn Phe
            260             265             270

AAC ATA CAA TAT GTC GCG CCG CAT CCC CGC CAG ACC TAC GGG CTT TCC     864
Asn Ile Gln Tyr Val Ala Pro His Pro Arg Gln Thr Tyr Gly Leu Ser
            275             280             285

GGC GTA ACC GCG TTA AAT TCG CCC TAT GTC ATC GAA GAC TAT ATT TTG     912
Gly Val Thr Ala Leu Asn Ser Pro Tyr Val Ile Glu Asp Tyr Ile Leu
        290             295             300

CGC GAA ATT AAG AAA AAC CCG CAT ACG AGG TAT GAA ATT TAT ACC TTT     960
Arg Glu Ile Lys Lys Asn Pro His Thr Arg Tyr Glu Ile Tyr Thr Phe
305             310             315                         320

TTC AGC GGT GCG GCG TTG ACG ATG AAG GAT TTT CCC AAT GTG CAC GTT    1008
Phe Ser Gly Ala Ala Leu Thr Met Lys Asp Phe Pro Asn Val His Val
                325             330             335

TAC GCA TTG AAA CCG GCT TCC CTT CCG GAA GAT TAT TGG CTC AAG CCC    1056
Tyr Ala Leu Lys Pro Ala Ser Leu Pro Glu Asp Tyr Trp Leu Lys Pro
            340             345             350

GTT TAT GCG CTG TTC CGT CAG GCC GAC ATT CCG ATT TTG ACA TTT GAC    1104
Val Tyr Ala Leu Phe Arg Gln Ala Asp Ile Pro Ile Leu Thr Phe Asp
            355             360             365

GAT AAA AAT TAA                                                    1116
Asp Lys Asn
        370
```

(2) INFORMATION FOR SEQ ID NO:4:

(i) SEQUENCE CHARACTERISTICS:
        (A) LENGTH: 371 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Leu Lys Lys Val Cys Leu Thr Val Leu Cys Leu Ile Val Phe
1               5                   10                  15

Cys Phe Gly Ile Phe Tyr Thr Phe Asp Arg Val Asn Gln Gly Glu Arg
            20                  25              30

Asn Ala Val Ser Leu Leu Lys Asp Lys Leu Phe Asn Glu Glu Gly Lys
            35              40              45

Pro Val Asn Leu Ile Phe Cys Tyr Thr Ile Leu Gln Met Lys Val Ala
    50              55                  60

Glu Arg Ile Met Ala Gln His Pro Gly Glu Arg Phe Tyr Val Val Leu
65              70                  75                      80

Met Ser Glu Asn Arg Asn Glu Lys Tyr Asp Tyr Phe Asn Gln Ile
                85              90                  95

Lys Asp Lys Ala Glu Arg Ala Tyr Phe Phe Tyr Leu Pro Tyr Gly Leu
            100             105             110

Asn Lys Ser Phe Asn Phe Ile Pro Thr Met Ala Glu Leu Lys Val Lys
            115             120             125

Ser Met Leu Leu Pro Lys Val Lys Arg Ile Tyr Leu Ala Ser Leu Glu
            130             135             140

Lys Val Ser Ile Ala Ala Phe Leu Ser Thr Tyr Pro Asp Ala Glu Ile
145             150             155                         160
```

-continued

```
Lys Thr Phe Asp Asp Gly Thr Asn Asn Leu Ile Arg Glu Ser Ser Tyr
                165                 170                 175
Leu Gly Gly Glu Phe Ala Val Asn Gly Ala Ile Lys Arg Asn Phe Ala
                180                 185                 190
Arg Met Met Val Gly Asp Trp Ser Ile Ala Lys Thr Arg Asn Ala Ser
                195                 200                 205
Asp Glu His Tyr Thr Ile Phe Lys Gly Leu Lys Asn Ile Met Asp Asp
            210                 215                 220
Gly Arg Arg Lys Met Thr Tyr Leu Pro Leu Phe Asp Ala Ser Glu Leu
225                 230                 235                 240
Lys Ala Gly Asp Glu Thr Gly Gly Thr Val Arg Ile Leu Leu Gly Ser
                245                 250                 255
Pro Asp Lys Glu Met Lys Glu Ile Ser Glu Lys Ala Ala Lys Asn Phe
                260                 265                 270
Asn Ile Gln Tyr Val Ala Pro His Pro Arg Gln Thr Tyr Gly Leu Ser
            275                 280                 285
Gly Val Thr Ala Leu Asn Ser Pro Tyr Val Ile Glu Asp Tyr Ile Leu
    290                 295                 300
Arg Glu Ile Lys Lys Asn Pro His Thr Arg Tyr Glu Ile Tyr Thr Phe
305                 310                 315                 320
Phe Ser Gly Ala Ala Leu Thr Met Lys Asp Phe Pro Asn Val His Val
                325                 330                 335
Tyr Ala Leu Lys Pro Ala Ser Leu Pro Glu Asp Tyr Trp Leu Lys Pro
                340                 345                 350
Val Tyr Ala Leu Phe Arg Gln Ala Asp Ile Pro Ile Leu Thr Phe Asp
            355                 360                 365
Asp Lys Asn
    370
```

(2) INFORMATION FOR SEQ ID NO:5:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..43
        (D) OTHER INFORMATION: /note= "5' primer SIALM-5F"

(xi) SEQUENCE DESCRIPTION: SEQ ID NO:5:

CTTAGGAGGT CATATGTTCA ATTTGTCGGA ATGGAGTTTT AGG        43

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..42
        (D) OTHER INFORMATION: /note= "3' primer SIALM-16R"

(xi) SEQUENCE DESCRIPTION: SEQ ID NO:6:

```
CCTAGGTCGA CTCATTAATT TTTATCGTCA AATGTCAAAA TC                                42
```

(2) INFORMATION FOR SEQ ID NO:7:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..78
        (D) OTHER INFORMATION: /note= "3' primer SIALM-18R"

(xi) SEQUENCE DESCRIPTION: SEQ ID NO:7:

```
CCTAGGTCGA CTCATTAGTT CAGGCTTTCT TCGCTGATCA GTTTTTGTTC ATTTTTATCG              60

TCAAATGTCA AAATCGGG                                                           78
```

(2) INFORMATION FOR SEQ ID NO:8:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..63
        (D) OTHER INFORMATION: /note= "5' primer SIALM-17R"

(xi) SEQUENCE DESCRIPTION: SEQ ID NO:8:

```
CCTAGGTCGA CTCATTAGTG GTGATGGTGG TGATGATTTT TATCGTCAAA TGTCAAAATC             60

GGG                                                                          63
```